United States Patent
Komura et al.

(10) Patent No.: US 11,064,941 B2
(45) Date of Patent: Jul. 20, 2021

(54) INFORMATION PROCESSING APPARATUS

(71) Applicant: FUJIFILM Business Innovation Corp., Tokyo (JP)

(72) Inventors: Akinori Komura, Kanagawa (JP); Katsunori Kawano, Kanagawa (JP); Minoru Mitsui, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 384 days.

(21) Appl. No.: 15/996,529

(22) Filed: Jun. 4, 2018

(65) Prior Publication Data

US 2019/0167185 A1 Jun. 6, 2019

(30) Foreign Application Priority Data

Dec. 6, 2017 (JP) .............................. JP2017-234491

(51) Int. Cl.
| | |
|---|---|
| *A61B 5/00* | (2006.01) |
| *A61M 21/00* | (2006.01) |
| *G16H 50/20* | (2018.01) |
| *A61B 5/0205* | (2006.01) |
| *A61B 5/16* | (2006.01) |
| *A61B 5/024* | (2006.01) |

(52) U.S. Cl.
CPC ............ *A61B 5/486* (2013.01); *A61B 5/0015* (2013.01); *A61B 5/02055* (2013.01); *A61B 5/165* (2013.01); *A61B 5/4035* (2013.01); *A61M 21/00* (2013.01); *G16H 50/20* (2018.01); *A61B 5/02438* (2013.01); *A61M 2230/06* (2013.01)

(58) Field of Classification Search
CPC .......... A61M 21/00; A61B 5/16; A61B 5/165; A61B 5/162; A61B 5/163; A61B 5/40; A61B 5/4035
See application file for complete search history.

(56) References Cited

U.S. PATENT DOCUMENTS

| | | | | |
|---|---|---|---|---|
| 2002/0051958 | A1* | 5/2002 | Khalsa | G09B 19/22 434/238 |
| 2006/0281543 | A1* | 12/2006 | Sutton | A61B 5/486 463/29 |
| 2008/0077619 | A1* | 3/2008 | Gilley | G09B 19/0092 |
| 2009/0123895 | A1* | 5/2009 | Hill | G09B 19/00 434/219 |

FOREIGN PATENT DOCUMENTS

| | | |
|---|---|---|
| JP | 2011081504 | 4/2011 |
| JP | 2016091490 | 5/2016 |

* cited by examiner

*Primary Examiner* — Samuel G Gilbert
(74) *Attorney, Agent, or Firm* — JCIPRNET

(57) ABSTRACT

An information processing apparatus includes a calculation unit, a designing unit, and a presentation unit. The calculation unit calculates autonomic activity of a participant, using biometric information measured by a measuring device that measures biometric information of the participant belonging to a group place. The designing unit designs a progress plan of communication at the group place in a design aspect corresponding to the calculated activity. The presentation unit presents the designed progress plan.

10 Claims, 12 Drawing Sheets

INFORMATION PROCESSING APPARATUS

CROSS-REFERENCE TO RELATED APPLICATIONS

This application is based on and claims priority under 35 USC 119 from Japanese Patent Application No. 2017-234491 filed Dec. 6, 2017.

BACKGROUND

Technical Field

The present invention relates to an information processing apparatus.

SUMMARY

According to an aspect of the invention, there is provided an information processing apparatus including a calculation unit that calculates autonomic activity of a participant, using biometric information measured by a measuring device that measures biometric information of the participant belonging to a group place; a designing unit that designs a progress plan of communication at the group place in a design aspect corresponding to the calculated activity; and a presentation unit that presents the designed progress plan.

BRIEF DESCRIPTION OF THE DRAWINGS

Exemplary embodiment(s) of the present invention will be described in detail based on the following figures, wherein.

DETAILED DESCRIPTION

1. Configuration

Figure 1:
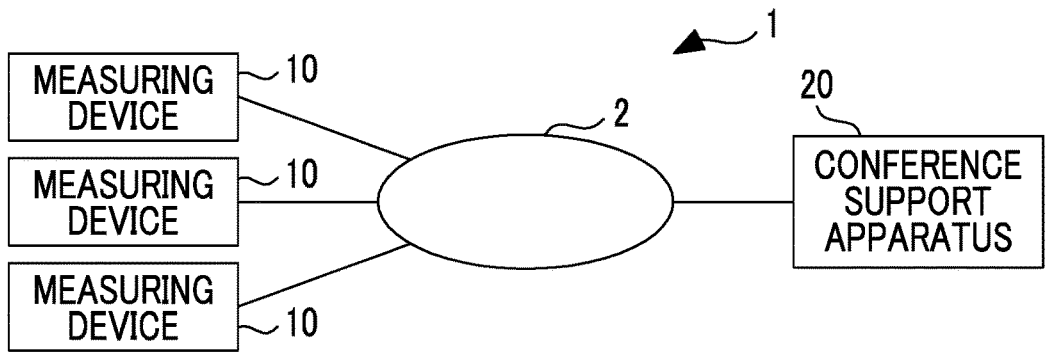
FIG. 1 is a diagram illustrating a configuration of a conference support system.

FIG. 1 is a block diagram illustrating a configuration of a conference support system 1 according to a present exemplary embodiment. The conference support system 1 is a system for supporting a conference performed by plural participants. The conference support system 1 includes plural measuring devices 10 and a conference support apparatus 20 (an example of an information processing apparatus). The measuring device 10 is a device that measures biometric information of an individual. The biometric information is various types of physiological and anatomical information emitted by a living body, and is information representing heart rate fluctuation, pulse waves, respiratory rates, or the like, for example. The measuring device 10 is, for example, a small heart rate sensor or a wrist watch-type heart rate sensor which performs measurement by sticking an electrode to a body. The conference support apparatus 20 is a computer device such as a smartphone, a tablet terminal, or a notebook personal computer (PC). The measuring device 10 is connected to the conference support apparatus 20 through a communication line 2. The communication line 2 includes at least one of, for example, the Internet, a mobile communication network, a telephone line, a local area network (LAN), or the like. Three measuring devices 10 are shown in FIG. 1, but the number of measuring devices 10 may be larger or smaller.

Figure 2:
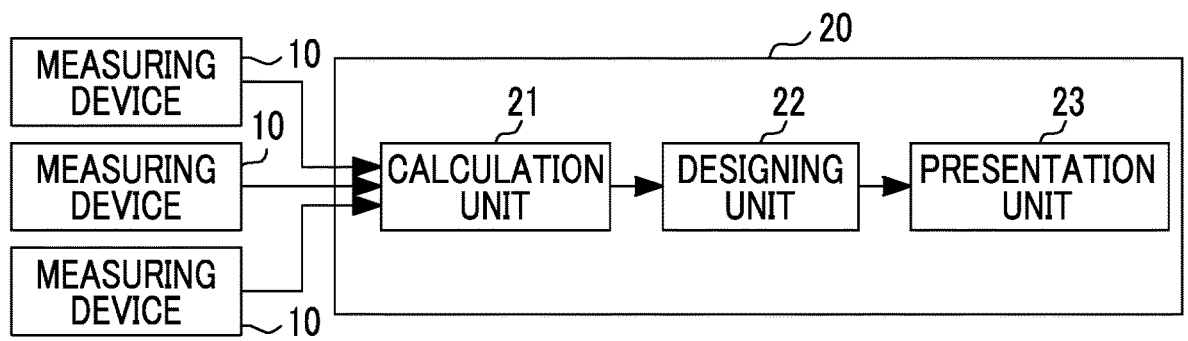
FIG. 2 is a diagram illustrating a functional configuration of the conference support system.

FIG. 2 is a block diagram illustrating the functional configuration of the conference support system 1. In FIG. 2, a calculation unit 21 calculates autonomic activity of a participant, using biometric information measured by the measuring device 10 that measures the biometric information of the participant belonging to a group place. A designing unit 22 designs a progress plan of communication at the group place in a design aspect corresponding to the activity calculated by the calculation unit 21. In the present exemplary embodiment, the group place is a place where plural people communicate with each other. The group place is, for example, a place of a conference performed by plural participants, or a place of a game played by plural participants. In addition, the group place may be, for example, an online video conference which is not face to face, or a place where there is a spatial gap. The presentation unit 23 presents the progress plan of the conference designed by the designing unit 22.

Figure 3:
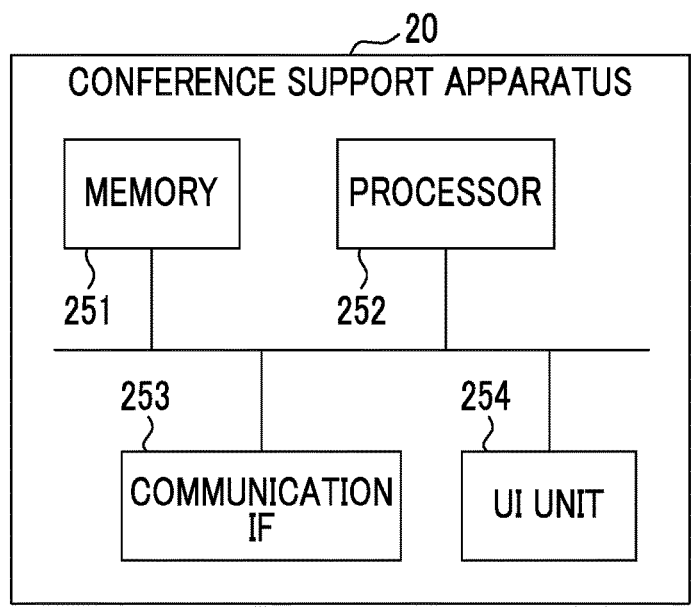
FIG. 3 is a diagram illustrating a hardware configuration of a conference support apparatus.

FIG. 3 is a diagram illustrating a hardware configuration of the conference support apparatus 20. In FIG. 3, a memory 251 stores various data. A processor 252 performs data processing according to a program stored in the memory 251. A communication IF 253 is an interface for performing data communication with an external device through a network. A UI unit 254 includes, for example, a touch screen and a key. The UI unit 254 may be built in the conference support apparatus 20 or may be externally attached and externally connected.

In this example, the function shown in FIG. 2 is implemented by the processor 252 executing the program stored in the memory 251. The processor 252 executing the program is an example of the calculation unit 21, the designing unit 22, and the presentation unit 23.

2. Operation

Next, the operation of the present exemplary embodiment will be described. In the following, as an example of a conference conducted by plural participants, a conference conducted by four participants (referred to as participants A, B, C, and D, respectively) will be described as an example.

Prior to start of the conference, each participant of the conference wears the measuring device 10 and the measurement of the biometric information is started. Each of the measuring devices 10 worn by the participants measures the biometric information at predetermined time intervals or in response to generation of a signal of biometric information such as heart rate and outputs the biometric information indicating the measurement result to the conference support apparatus 20.

Figure 4:
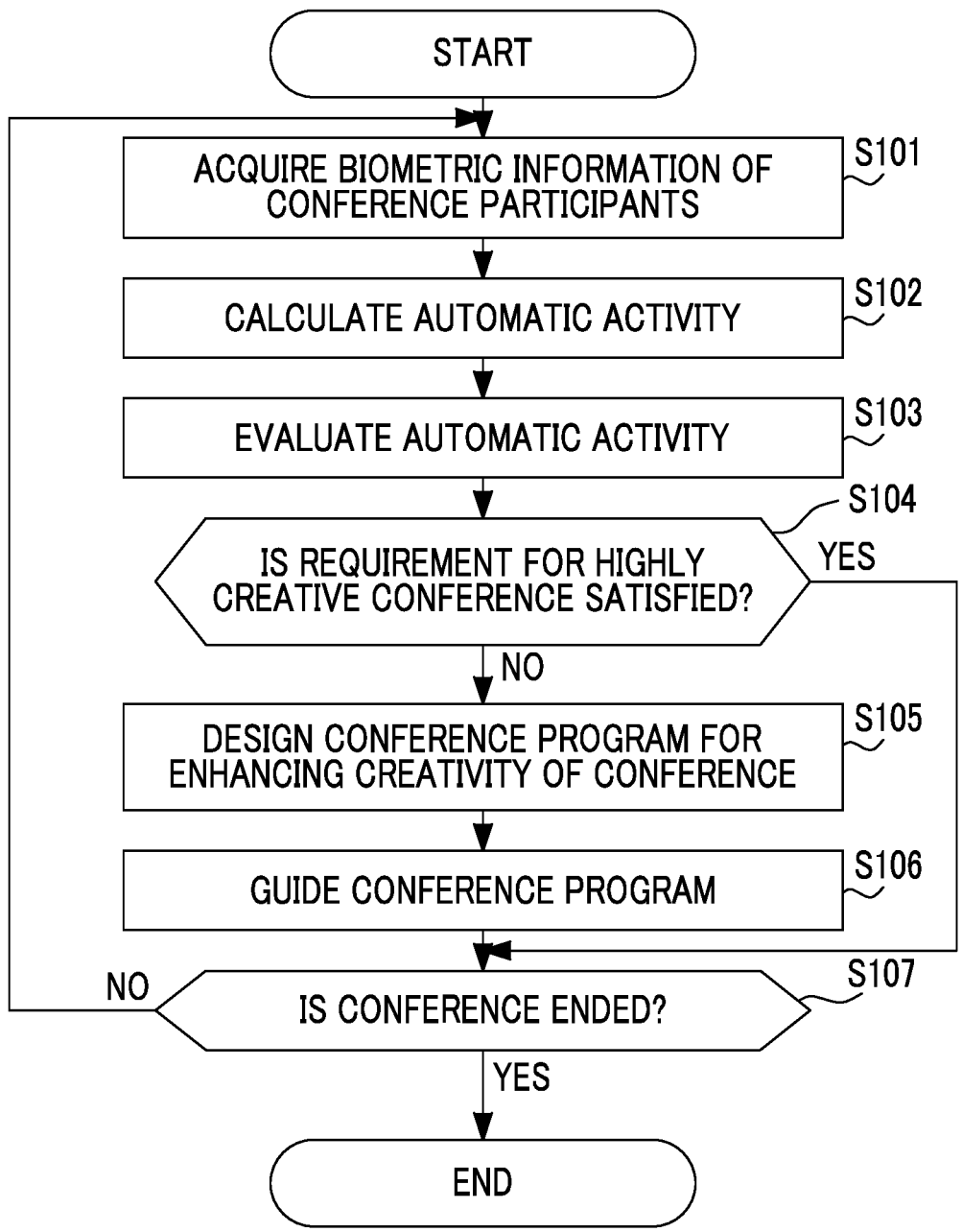
FIG. 4 is a flowchart illustrating an operation flow of the conference support system.

FIG. 4 is a flowchart illustrating the operation in the present exemplary embodiment. In step S101, the calculation unit 21 acquires the biometric information measured by the measuring device 10. In step S102, the calculation unit 21 calculates the activity degree (hereinafter simply referred to as "activity") of automatic nerve based on the biometric information acquired in step S101. In the present exemplary embodiment, total autonomic activity (TP), sympathetic activity (LF/HF), and parasympathetic activity (HF) are calculated as the activities. For these calculation methods, a generally known method is used. Specifically, for example, TP is a cumulative intensity in the entire frequency range (for example, 0.01 to 0.4 Hz) in a case where a heart rate fluctuation with a predetermined time width is subjected to fast Fourier transformation. LF/HF is the ratio of the cumulative intensity in a low frequency range (for example, 0.04 to 0.15 Hz) to the cumulative intensity in a high frequency range (for example, 0.15 to 0.4 Hz). HF is the cumulative intensity in a high frequency range (for example, 0.15 to 0.4 Hz).

Note that each activity is not limited to this. In addition to the above indicators, for example, it is also possible to use CVRR as total autonomic activity, ccvLF/HF, LF, ccvLF as sympathetic activity, ccvHF as parasympathetic activity, and the like.

In step S103, the calculation unit 21 compares the value of activity necessary for realizing a high-creativity conference with the value of the activity before starting or during implementation of a target conference and evaluate whether or not the conference has reached a state of high creativity. In the present exemplary embodiment, in a case where the TP is equal to or larger than the predetermined threshold, it is evaluated that the creativity of the conference is high. Specifically, the calculation unit 21 determines a reference value of the TP that realizes a high-creativity conference, using a reference value table prepared based on measurement results of creativity of various conferences, and compares the value with the activities of target conferences.

The reference value table is generated as follows, for example. As a result of intense research, the present inventors have found that the creativity of the conference is high in a case where conference participants have high TP. With respect to creativity, the timing when an individual feels high creativity during the conference is measured, and the activity at that timing is calculated and compared. There are individual differences in activity at a timing when the participants feel high creativity, so creativity is distributed with a width.

Figure 5:
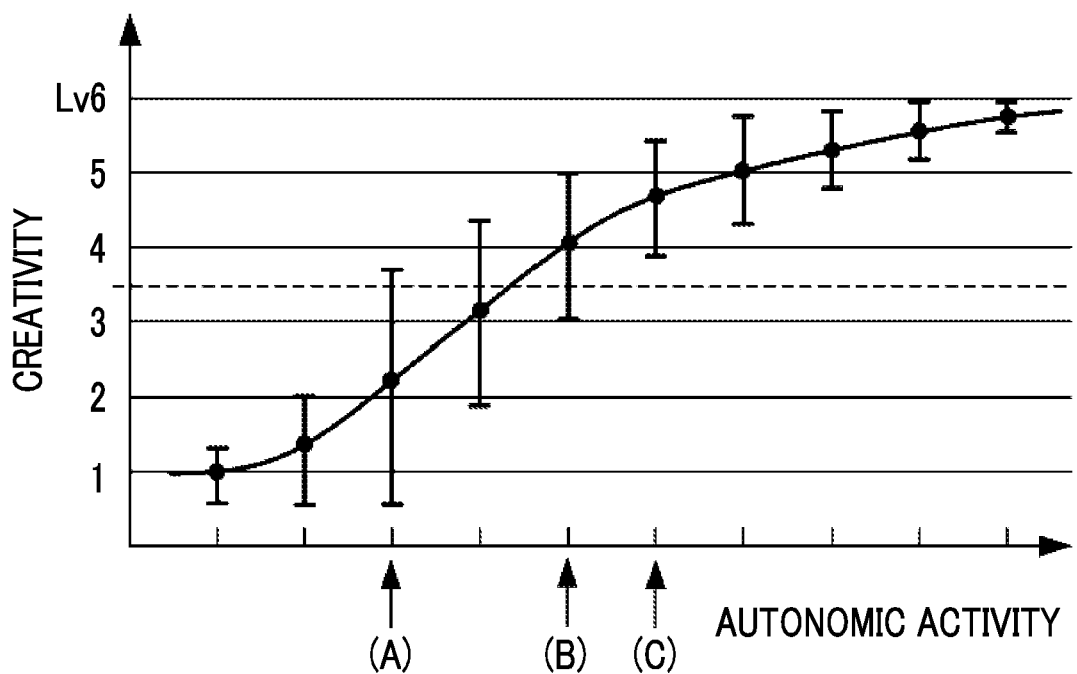
FIG. 5 is a diagram illustrating a relationship between autonomic activity and a height of creativity.

FIG. 5 is a diagram schematically showing a relationship between the activity and the subjective evaluation of the height of creativity. The height of creativity is evaluated in 6 levels according to the individual's sense, and regarding the measurement result of activity at the conference at that time, the standard deviation for variations in the evaluation results of creativity in one activity is indicated by error bars. With respect to the evaluation of creativity, for example, it is more preferable to obtain answers indicating specific criteria such as "Lv6: New behavior is checked", "Lv5: New means is proposed", "Lv4: There are new awareness, and discovery", "Lv3: It is only an introduction to general theory and existing knowledge", "Lv2: Talk does not proceed forward only by presenting problems and reasons why it cannot be done", and "Lv1: Talk turns back only by understanding the current situation and checking the location of responsibility".

In FIG. 5, when it is determined that Lv6 to Lv4 are in a state of high creativity (Lv3 to Lv1 are in a state of low creativity), at the intermediate point of Lv3 and Lv4, there are (A) a method in which the activity when the highest point of the variation of the evaluation value of the creativity exceeds the intermediate point is taken as a threshold, (B) a method in which the activity when the central value of the variation of the evaluation value of the creativity exceeds the intermediate point is taken as a threshold, and (C) a method in which the activity when the lowest point of the variation of the evaluation value of the creativity exceeds the intermediate point is taken as a threshold.

Unlike highly efficient or highly productive conferences, highly creative conferences may need a state where at least one of the participants can speak creative speech. Therefore, after measuring TP of all participants, a participant having the highest TP value during the conference may be controlled. That case corresponds to using the minimum value as the reference TP and using the threshold determined by the method (A). In addition, for example, it is preferable that more than half of the participants are in a state of high creativity, and that case corresponds to using the average value as the reference TP and using the threshold determined by the method (B). At this time, since there are plural participants who are in a state of high creativity, interaction occurs and the creativity of the whole conference place is increased. Furthermore, for example, it is preferable that all the participants are in a state of high creativity, and that case corresponds to using the maximum value as the reference TP and using the threshold determined by the method (C).

Further, the TP is not high over the duration of the conference, a great rise in TP occurs with a few minutes of width, causing a state of high creativity around it. Therefore, the average value or the maximum value in the predetermined time width up to time t is used for TP at time t used for determination. More specifically, a measurement value of at least one minute, for example, a measurement value in a section of three minutes or more is used. Further, the maximum value may be selected for the TP value of the measurement section.

Figure 6:
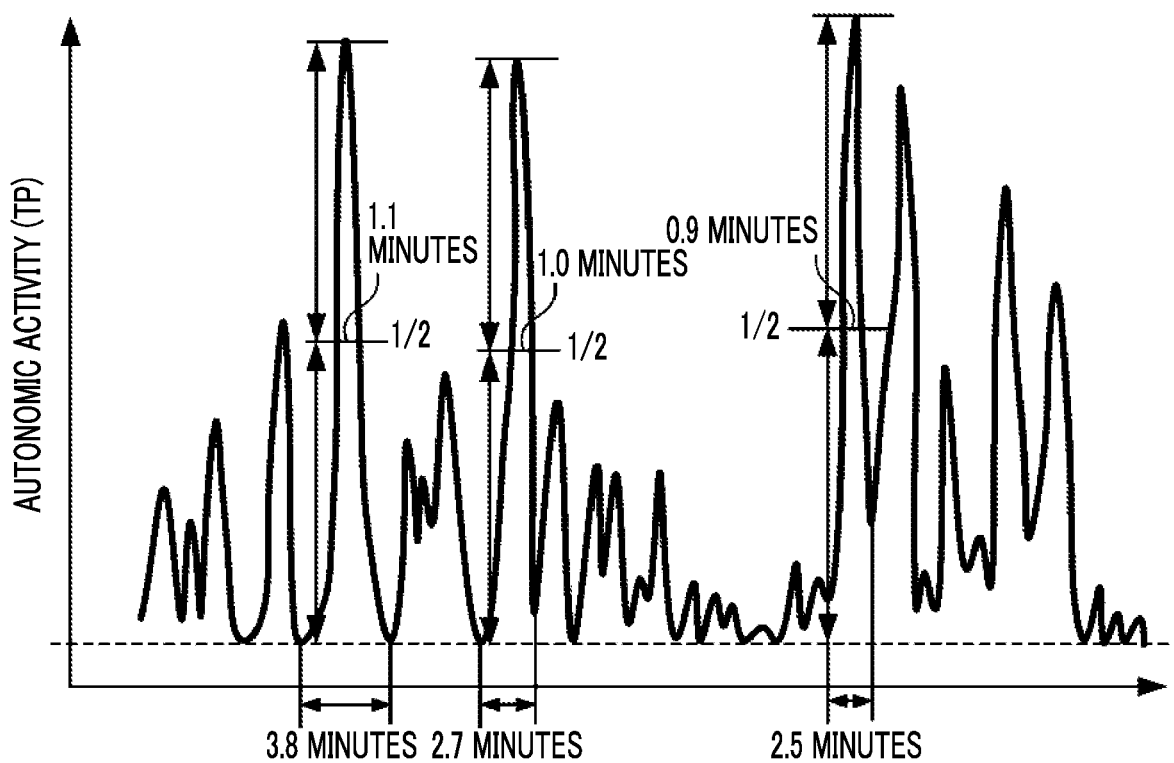
FIG. 6 is a diagram illustrating a value of autonomic activity corresponding to an elapsed time of a conference.

FIG. 6 is a graph showing the value of TP corresponding to an elapsed time of the conference. As shown in FIG. 6, the value of TP shows a sharp rise around the state of high creativity, but it takes about three minutes from the start of the rise to attenuation to the steady state. Therefore, for example, it is desirable to evaluate a psychological change when the participant feels creativity for three minutes. In addition, since the value of TP exceeds half of the maximum value in the rise of TP at about one minute, the evaluation may be performed for at least one minute.

Return to the description of FIG. 4. In steps S104 to S106, in a case where the calculated TP of participants in the conference does not satisfy the requirement of TP necessary for making a highly creative conference, the designing unit 22 presents a progress process to optimize the conference program to adjust the TP. The requirement of TP for highly creative conference is, for example, a requirement that the time length over which the TP value exceeds the threshold is equal to or greater than a predetermined rate.

First, in step S104, the designing unit 22 determines based on the evaluation result of step S103 whether the requirement for highly creative conference is satisfied (whether the measured TP exceeds a preset threshold or the like). In a case where it is determined that the creativity of the conference is high (YES in step S104), the designing unit 22 skips the processes of steps S105 and S106 and proceeds to the process of step S107. On the other hand, in a case where it is determined that the creativity of the conference is not high (NO in step S104), the designing unit 22 proceeds to the process of step S105.

In step S105, the designing unit 22 designs a conference program for enhancing the creativity of the conference. In the present exemplary embodiment, a conference program composed of the following five conference menus is used as a conference program.

STEP 1 (Check-In): As self-introduction, participants speak frankly about their feelings at the current time one by one.

STEP 2 (Pair Dialogue): Two participants form one pair, they talk about individual thoughts on the agenda and know each other.

STEP 3 (Other Participant Introduction): Two pairs of four participants are one group, they each explain the thought of the opponent heard in STEP 2 to other participants.

STEP 4 (World Cafe): four people gather to form one group and discuss the resolution idea of the agenda.

STEP 5 (Check-Out): Talk one by one the new awareness obtained at this conference.

The conference menu in a case of conducting highly creative conferences has the effect of improving TP originally. As a method of designing a conference to adjust TP, for example, methods such as extending the time of the conference menu, repeating one conference menu plural times, changing constituent members of the conference menu, and the like are used. Specifically, in this exemplary embodiment, contents are changed on conference menus of pair dialogue (storytelling and story retelling) for talking about their own thought and listening to the story of the opponent, a world cafe which is a group dialogue, or the like.

Figure 7:
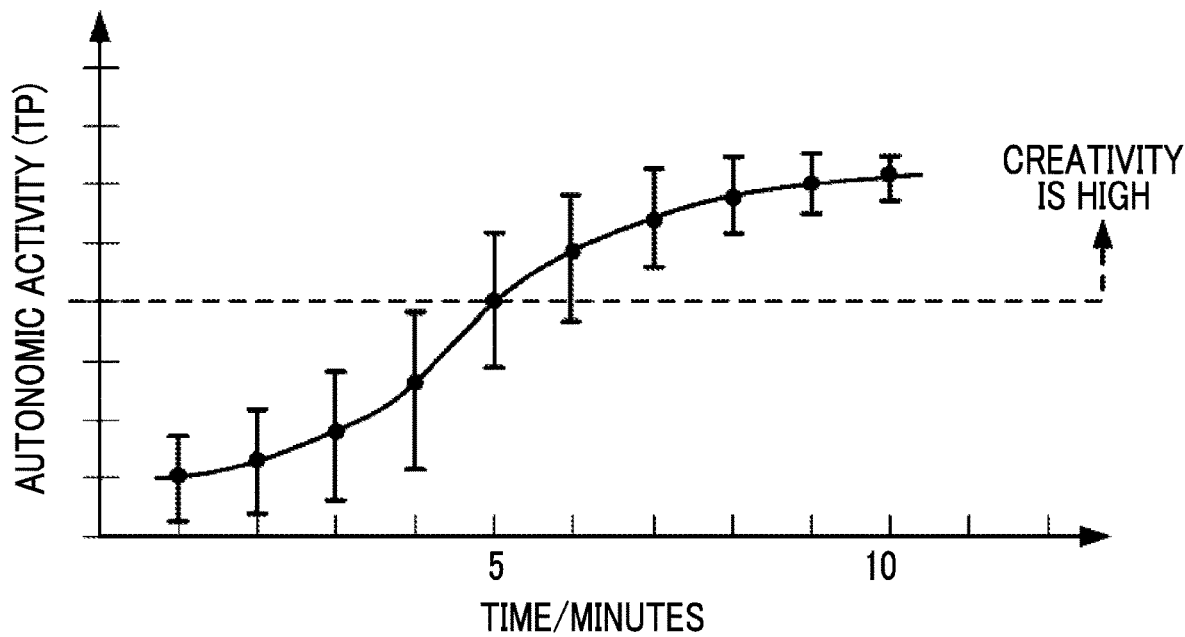
FIG. 7 is a graph showing a relationship between a dialogue time and a height of autonomic activity, for a pair dialogue according to an exemplary embodiment of the present invention.

FIG. 7 is a graph showing a relationship between the dialogue time and the height of the autonomic activity for a pair dialogue. In FIG. 7, the horizontal axis represents time and the vertical axis represents the value of TP. As can be seen from this graph, the longer the dialogue time is, the higher the value of the autonomic activity tends to increase. As a representative example, it can be seen that the timing when the creativity is high (the average value of TP exceeds the threshold) is around 5 minutes. As the time of a pair dialogue increases, the value of TP increases and the variation decreases, but the maximum value may not increase to the extent that the creativity level reaches the maximum (Lv6).

Figure 8:
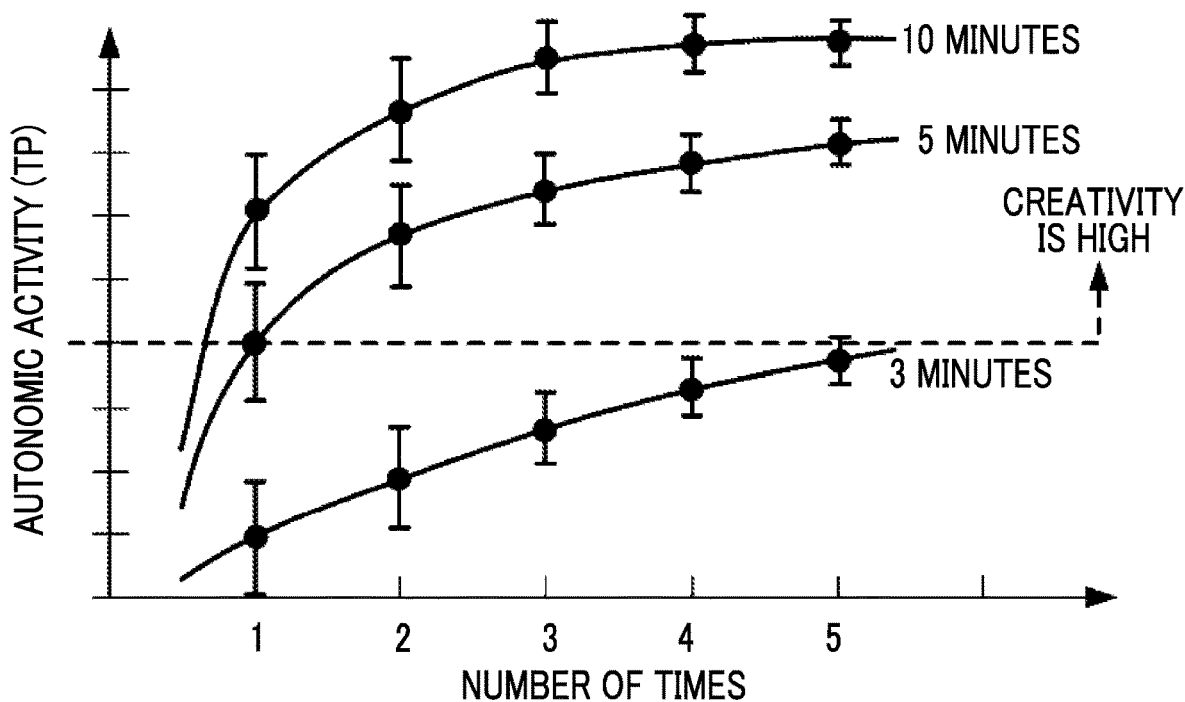
FIG. 8 is a graph showing a relationship between the number of dialogues and a height of autonomic activity, for the pair dialogue according to the exemplary embodiment of the present invention.

FIG. 8 is a graph showing a relationship between the number of dialogues and the height of the autonomic activity for a pair dialogue. In FIG. 8, the horizontal axis represents the number of dialogues and the vertical axis represents the value of TP. According to this graph, it is shown that the value of autonomic activity tends to increase as the number of dialogues increases. Further, the longer the dialogue time is, the faster the value increases. As a representative example, it can be seen that the number of dialogues with high creativity (the average value of TP exceeds the threshold) is 1 in a case where the dialogue is about 5 minutes or longer. As the number of pair dialogue increases, the value of TP increases and the variation decreases, and in a case where the time of one dialogue is long (for example, 10 minutes or the like), the maximum value may reach the highest creativity level (Lv6).

Figure 9:
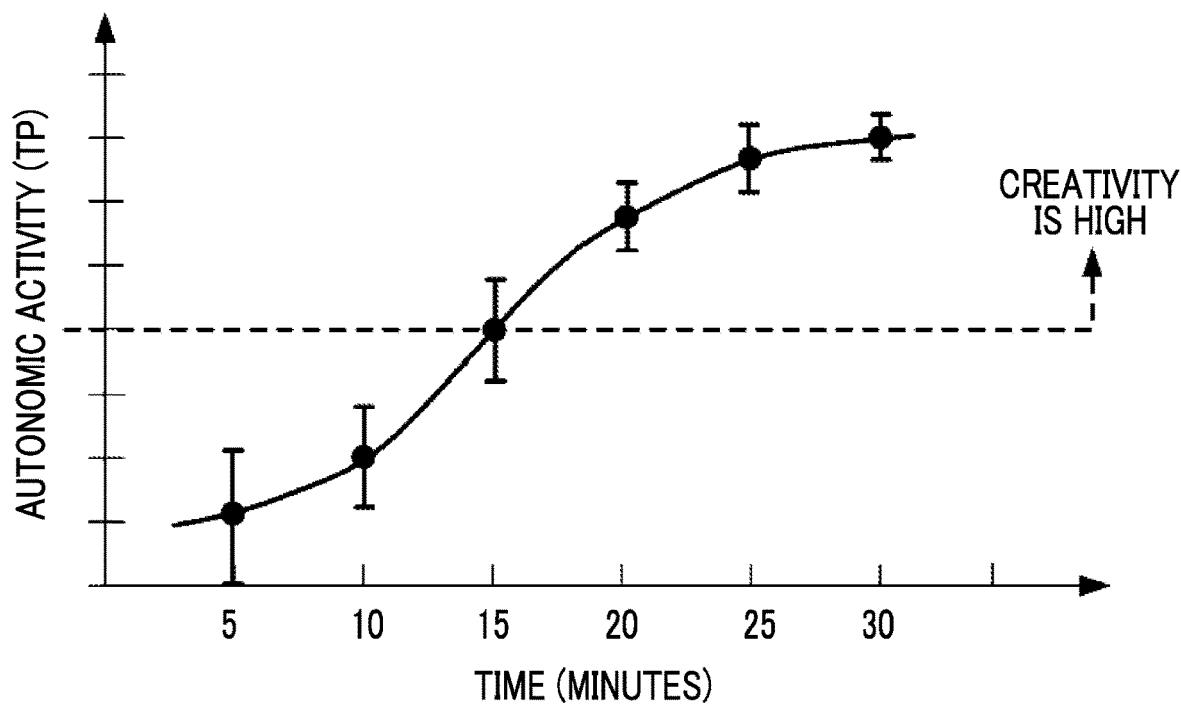
FIG. 9 is a graph showing a relationship between a dialogue time and a height of autonomic activity, for a group dialogue according to the exemplary embodiment of the present invention.

FIG. 9 is a graph showing a relationship between the dialogue time and the height of the autonomic activity for a group dialogue. According to this graph, it is shown that the value of autonomic activity tends to increase as the dialogue time is longer. As a representative example, it can be seen that the timing when the creativity is high (the average value of TP exceeds the threshold) is around 15 minutes. As the time of a group dialogue increases, the value of TP increases and the variation decreases, and the maximum value approaches the highest creativity level (Lv6).

Figure 10:
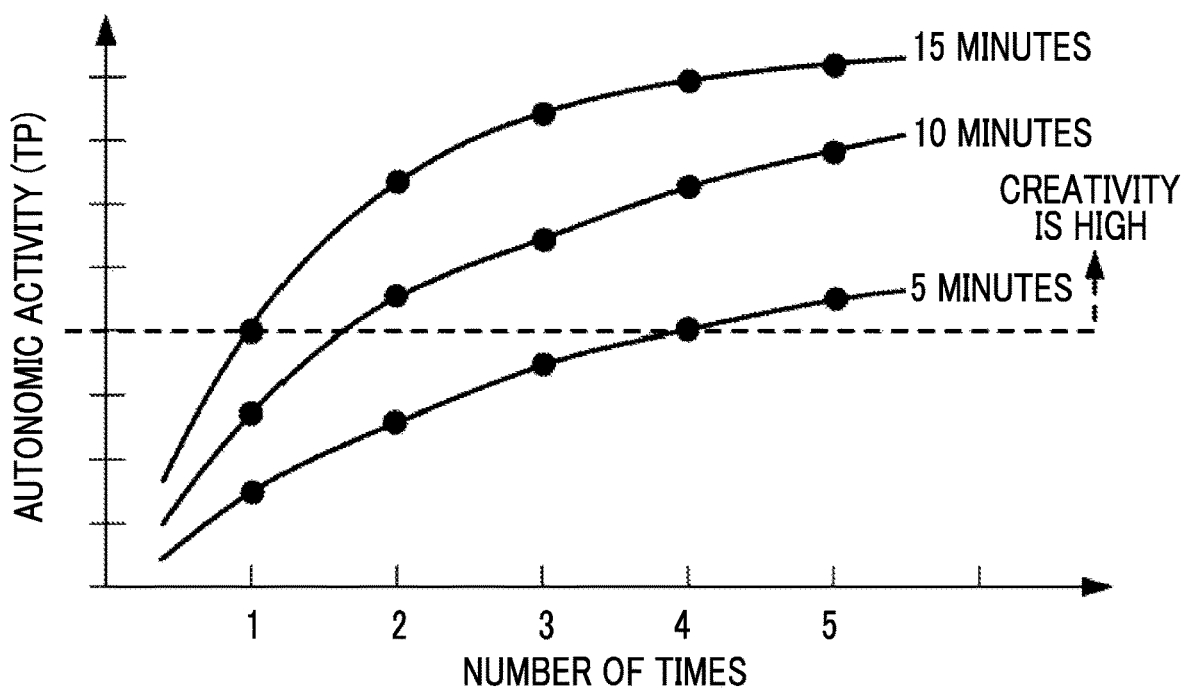
FIG. 10 is a graph showing a relationship between the number of dialogues and a height of autonomic activity, for the group dialogue according to the exemplary embodiment of the present invention.

FIG. 10 is a graph showing a relationship between the number of dialogues and the height of the autonomic activity for a group dialogue. According to this graph, it is shown that the value of autonomic activity tends to increase as the number of dialogues increases. Further, the longer one dialogue time is, the faster the rise occurs. As a representative example, it can be seen that the number of dialogues at which the creativity is high (the average value of TP exceeds the threshold) is 2 in a case where the dialogue is about 10 minutes or longer. As the number of group dialogue increases, the value of TP increases and the variation decreases, and in a case where the time of one dialogue is long (for example, 15 minutes or the like), the maximum value may reach the highest creativity level (Lv6). In comparison with the cumulative dialogue time, the longer one dialogue time is, the faster the value of TP tends to rise.

Return to the description of FIG. 4. The designing unit 22 designs the progress plan of the conference in the design aspect corresponding to the activity calculated in step S102. In the present exemplary embodiment, the conference progress plan refers to the combination of items included in the conference, the progress order of the conference items, the configuration of the participating members, and the content of the conference items included in the conference. In the present exemplary embodiment, the designing unit 22 performs a process for specifying at least one of the time, number of repetitions, participants, or agenda of conference items (menus) included in the conference. For example, a conference progress plan is designed such as to lengthen the time length of a specific menu included in the conference, to repeat a specific menu plural times, to change the combination of participants, and to change the number of participants. As described above, in a case where it is determined that the TP of the conference participants obtained by the calculation unit 21 has not reached a desired value, based on the relationship between the above-described TP and the conference program, regarding plural menus having the effect of adjusting the autonomic activity included in the conference program, the designing unit 22 designs implementation conditions that adjust the time, number of times, or the like of at least some conference menus.

In step S106, the presentation unit 23 presents the progress plan of the conference designed in step S105, and guides the conference program. In the present exemplary embodiment, the presentation unit 23 presents an implementation condition for adjusting the time, number of times, or the like of each conference menu indicated by the designing unit in order to implement a highly creative conference in the implementation of each conference menu.

As a method of presenting the conference program by the presentation unit 23, in addition to displaying the conference program on the UI unit 254 of the conference support apparatus 20, for example, the following method can be adopted. For example, a display is installed at a position where participants in the conference hall can see, and an instruction on the method of implementing the conference menu may be presented there. In a case where there is a moderator in the hall, the display content may be verbally instructed by the moderator. Meanwhile, the role of moderator of the conference may be executed by programmed AI. Further, the display contents may be presented from the speaker by a machine voice or the like. In addition, since the instruction is presented by sentences and figures, the instruction may be autonomously performed with reference to the method in which the conference participants are displayed, based on the cue representing the break of the conference menu such as a chime. The contents of this instruction may be displayed on a small display such as a wristwatch type display, a mobile phone, and a smartphone possessed by a moderator and announced. For example, a PC that presents instruction contents is connected to a display and a speaker installed in the hall by a cable, and the presenting of the contents may be realized by transmitting the progress method determined by the designing unit 22 in the PC to the guiding units. On the other hand, in the case of a portable device, it may be wirelessly connected by WiFi connection, Bluetooth (registered trademark), or the like.

As a result of intensive research, the present inventors have found that there is a process necessary for adjusting autonomic nerves in a case of forming a state where the participant's TP for practicing high-creative conference is high. In the present exemplary embodiment, the designing unit 22 designs a progress process optimizing the conference program to adjust the TP in advance before implementation of the conference menu, in a case where the autonomic activity requirement necessary for conducting a highly creative conference is not satisfied, based on the autonomic activity of the participant before the conference calculated by the calculation unit 21.

More specifically, it is easy for a highly creative conference to be held, by increasing autonomic activity to an appropriate level in order of suppressing the sympathetic activity to relieve tension at the start of the conference, next, enhancing parasympathetic activity to deepen mutual understanding, and then enhancing all autonomic nerves to conduct creative discussion. Therefore, before starting the conference menu, a mental and physical condition adjustment program for adjusting the autonomic activity is presented so as to satisfy the requirement of the autonomic activity necessary for performing a highly creative conference. The mental and physical condition adjustment program is physical exercise such as meditation, breathing method (such as deep breathing), and flexible exercise (such as yoga). Unlike sensory stimulation, physical exercise affects directly the change of autonomic nerves, so individual differences are small.

Figure 11:
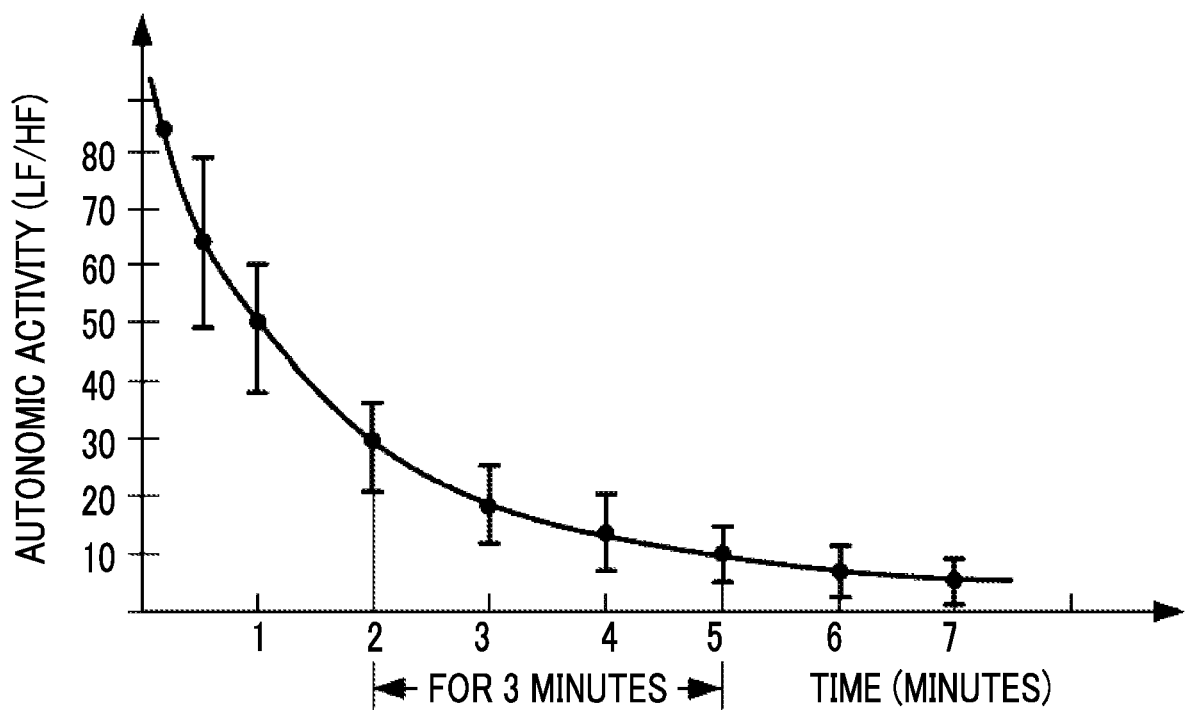
FIG. 11 is a schematic diagram showing a change in autonomic activity by meditation.

FIG. 11 is a diagram showing changes in autonomic activity by meditation. In FIG. 11, the horizontal axis represents time and the vertical axis represents the value of sympathetic activity. The physical exercise has an effect of suppressing the sympathetic nerve. Therefore, it acts effectively as a preparation to lead a participant whose sympathetic nerve is enhanced in a state of tension to a state of high creativity. A breathing method having a similar effect may be utilized. How the LF/HF varies over time from the initial value is collectively represented as a single graph. In a case where different graphs are generated for each value of LF/HF with different initial values, the variation at each elapsed time becomes smaller and more detailed control is performed.

Figure 12A:
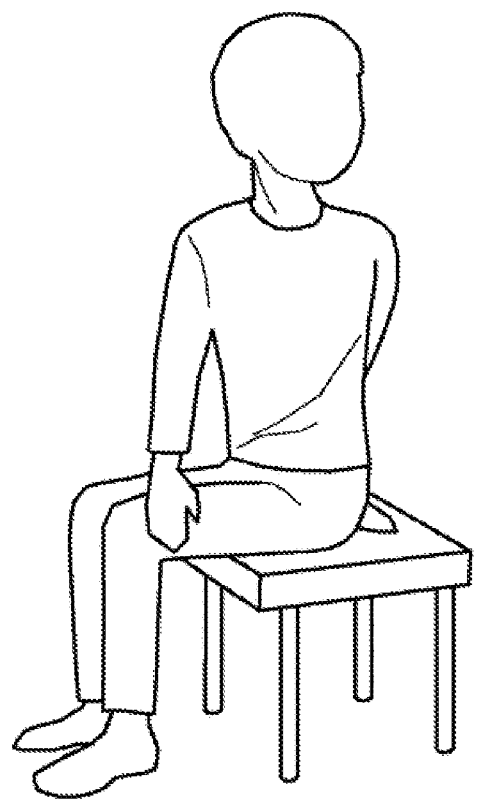
FIGS. 12A and 12B are schematic diagrams showing a method of implementing flexible exercises for suppressing sympathetic nerve according to the exemplary embodiment of the present invention.
Figure 12B:
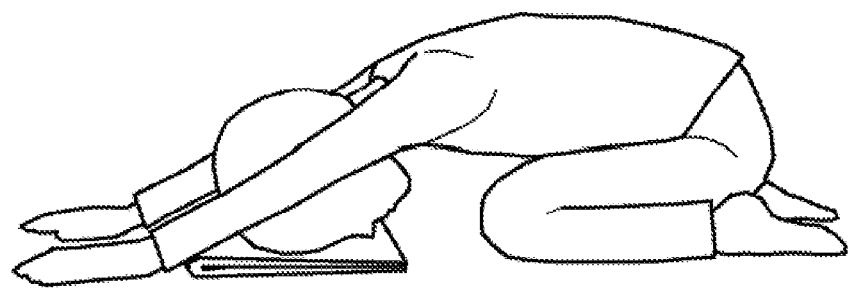
Figure 13:
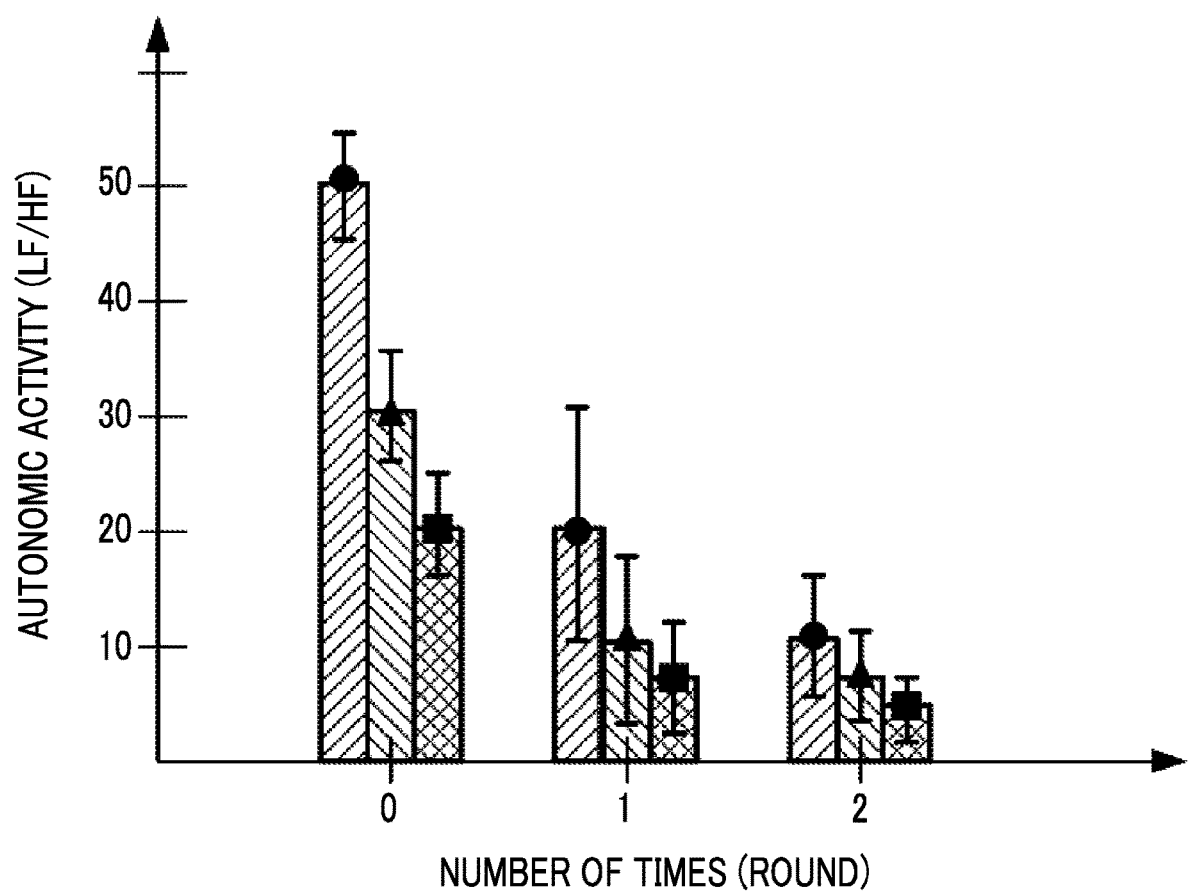
FIG. 13 is a schematic diagram showing a change in sympathetic activity by flexible exercise according to the exemplary embodiment of the present invention.

FIGS. 12A and 12B are diagrams illustrating a method of implementing flexible exercises for suppressing sympathetic nerves, and FIG. 13 is a diagram illustrating a change in sympathetic activity by the flexible exercises illustrated in FIGS. 12A and 12B. As exemplified in FIGS. 12A and 12B, FIGS. 14A and 14B, and FIGS. 16A and 16B, physical exercise has three types of movement patterns having an action of suppressing sympathetic nerve, an action of enhancing parasympathetic nerve, action of enhancing sympathetic nerve. Through these actions, the conference process to conduct highly creative conferences proceeds in order of relieving participants' tension, increasing susceptibility and increasing creativity.

At the beginning of the conference, many participants become tense and sympathetic nerves are in a state of enhanced. Then, in STEP 1, the sympathetic nerve is suppressed in order to generate a secure and safe place and induce a relaxation mode for relaxing the tension. Representative flexible exercise used here include "twisting pose" which is performed by sitting in a chair, "child pose" which is performed by sitting on the floor, or the like, as shown in FIGS. 12A and 12B. FIG. 13 exemplifies the suppression effect of LF/HF in a case where these flexible exercises are performed. In a case where the average value in the initial state is different, the LF/HF suppression effect by the flexible exercise is also different. In the example of FIG. 13, with respect to the case where the initial values are 50, 30, and 20, the values of LF/HF after execution of first time and after execution of second time are shown, with the value before execution as 0. The duration of one flexible exercise is expected to be 30 seconds. From FIG. 13, it can be seen that a specific flexible exercise acts to suppress LF/HF.

Figure 14A:
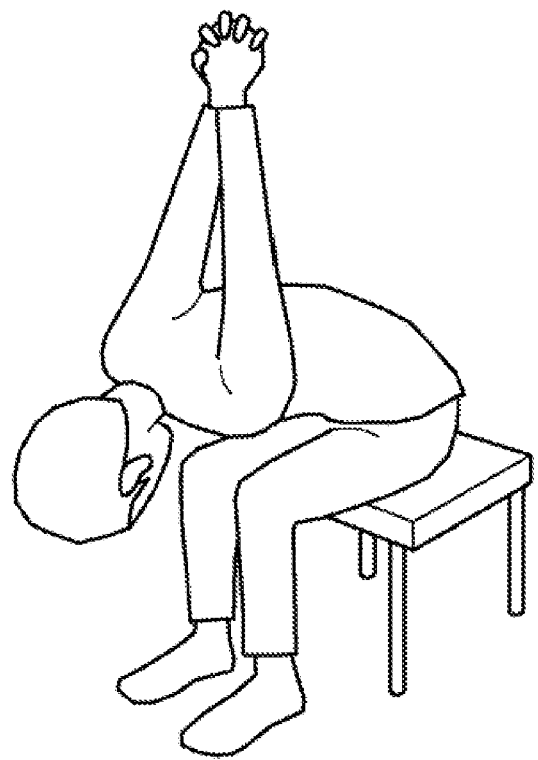
FIGS. 14A and 14B are schematic diagrams showing a method of implementing flexible exercises for enhancing parasympathetic nerve according to the exemplary embodiment of the present invention.
Figure 14B:
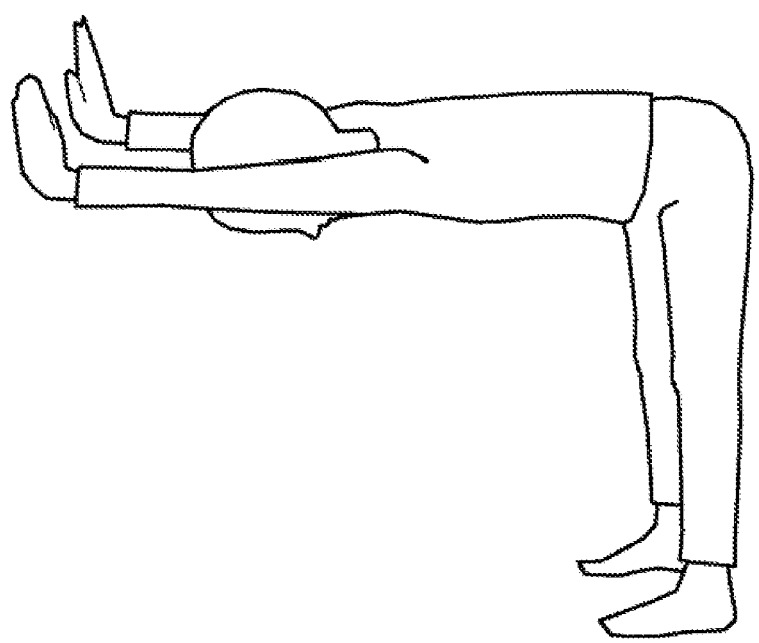
Figure 15:
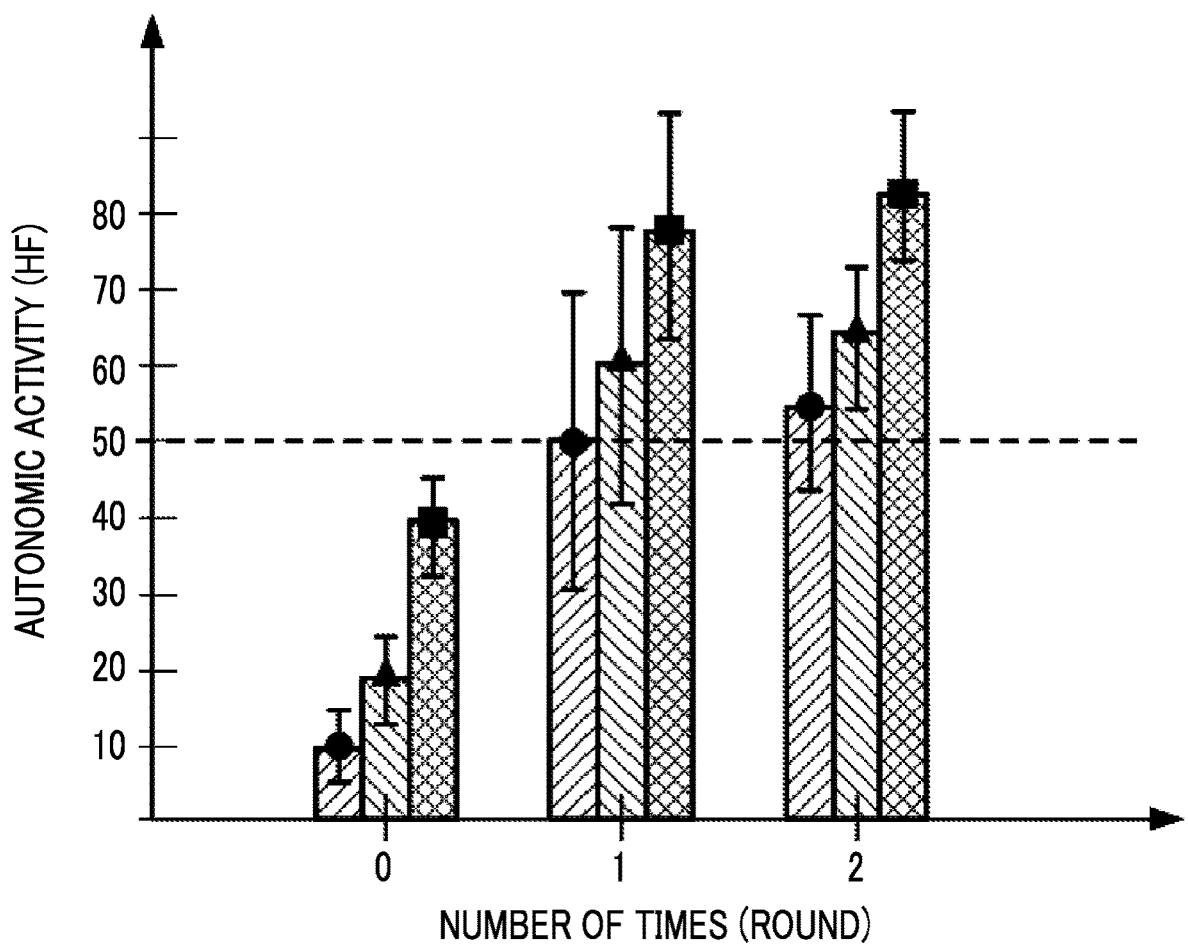
FIG. 15 is a schematic diagram showing a change in parasympathetic activity by flexible exercise according to the exemplary embodiment of the present invention.

FIGS. 14A and 14B are diagrams illustrating a method of implementing a flexible exercise for enhancing parasympathetic nerve, and FIG. 15 is a diagram illustrating a change in the parasympathetic activity by the flexible exercise. In the present exemplary embodiment, the parasympathetic nerve is enhanced in order to induce a refresh mode preparing for listening in STEP 2. Representative flexible exercise used here include "half tortoise pose" which is performed by sitting in a chair, "downward-facing dog pose" which is performed by standing on the floor, or the like, as shown in FIGS. 14A and 14B. The enhancement effect of HF in a case where these flexible exercises are performed is illustrated in FIG. 15. In a case where the average value in the initial state is different, the HF enhancement effect by the flexible exercise is also different. In the example of FIG. 15, with respect to the case where the initial values are 10 ms^2, 20 ms^2, and 40 ms^2, the values after execution of first time and after execution of second time are shown, with the value before execution as 0. The duration of one flexible exercise is expected to be 30 seconds. From FIG. 15, it can be seen that a specific flexible exercise acts to enhance LF/HF.

Figure 16A:
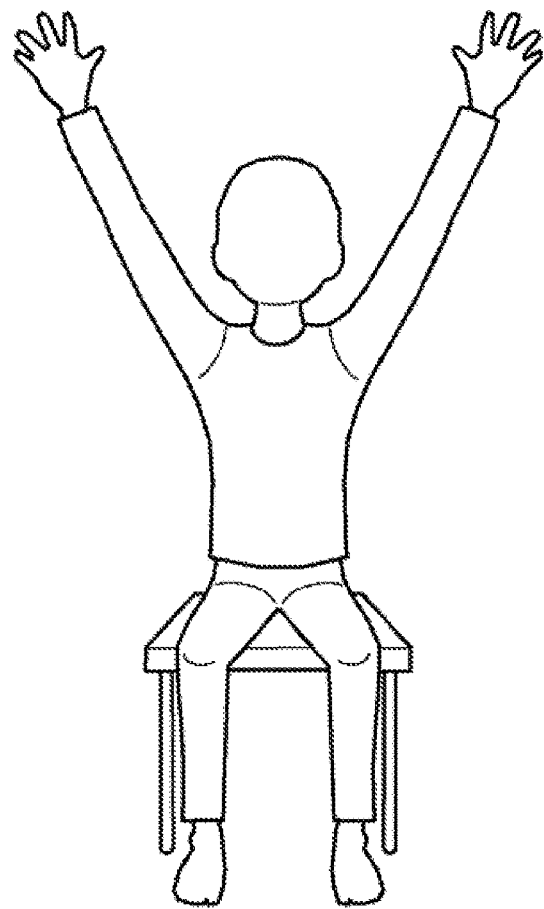
FIGS. 16A and 16B are schematic diagrams showing a method of implementing flexible exercises for enhancing sympathetic nerve according to the exemplary embodiment of the present invention.
Figure 16B:
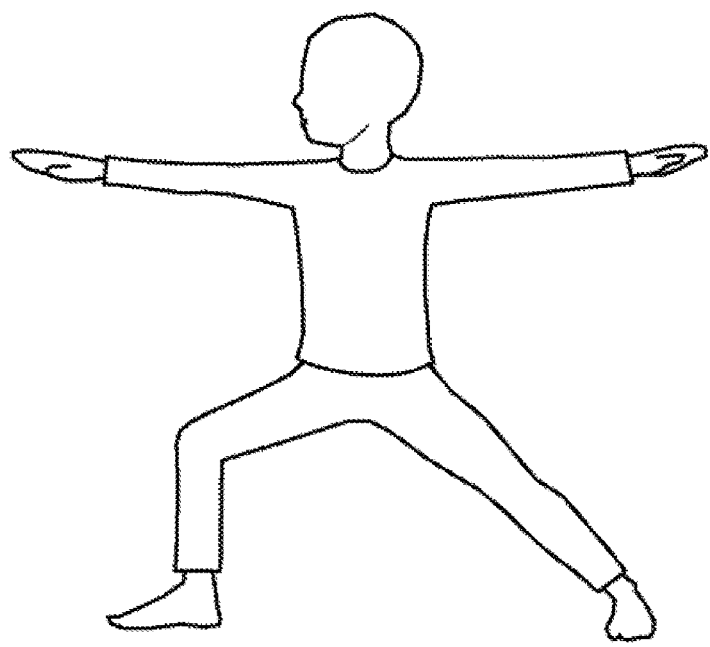
Figure 17:
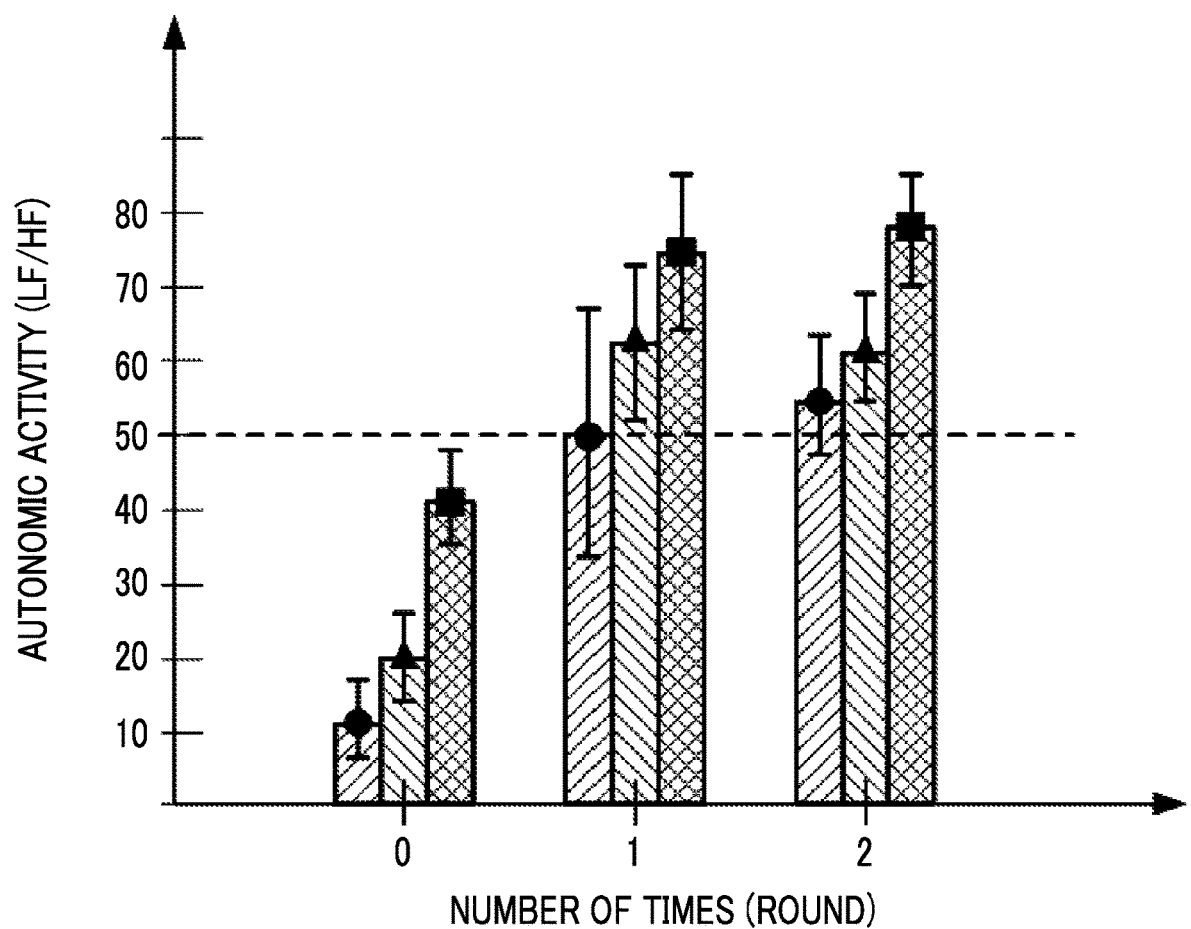
FIG. 17 is a schematic diagram showing a change in sympathetic activity by flexible exercise according to the exemplary embodiment of the present invention.

FIGS. 16A and 16B are diagrams illustrating a method of implementing a flexible exercise for enhancing sympathetic nerve, and FIG. 17 is a diagram illustrating a change in the sympathetic activity by the flexible exercise. In the exemplary embodiment, sympathetic nerve is enhanced in order to induce an energetic mode preparing for talking openly in STEP 4. Representative flexible exercise used here include "antenna pose" which is performed by sitting in a chair, "hero pose" which is performed by standing on the floor, or the like, as shown in FIGS. 16A and 16B. FIG. 17 exemplifies the enhancement effect of LF/HF in a case where these flexible exercises are performed. In a case where the average value in the initial state is different, the LF/HF enhancement effect by the flexible exercise is also different. In the example of FIG. 17, with respect to the case where the initial values are 10, 20, and 40, the values after execution of first time and after execution of second time are shown, with the value before execution as 0. The duration of one flexible exercise is expected to be 30 seconds. From FIG. 17, it can be seen that a specific flexible exercise acts to enhance LF/HF.

When the value of the autonomic activity necessary for starting the next conference menu has not been reached in a case where each conference menu is ended, the designing unit 22 sets implementation of physical exercise menu. The presentation unit 23 presents information on an implementation method which is set.

Return to the description of FIG. 4. In step S107, the presentation unit 23 determines whether the conference is ended. In a case where it is determined that the conference has ended (YES in step S107), the presentation unit 23 ends the process. On the other hand, in a case where it is determined that the conference is not ended (NO in step S107), the presentation unit 23 returns to the process of step S101.

3. Operation Example 3-1. Operation Example 1 (Extension Only by Extrapolation Time)

Hereinafter, as an operation example of the present invention, a specific example guiding a conference to be a highly creative conference in a case where the conference with four participants A, B, C, and D is held will be described.

In this operation example, each of four participants wears the measuring device 10 before start of the conference. The biometric information acquired by the measuring device 10 is transmitted to the conference support apparatus 20 by radio communication or wire communication at intervals of approximately several seconds according to the sensing performance of the sensor of the measuring device 10. The conference support apparatus 20 calculates the autonomic activity (for example, TP, HF, LF/HF, or the like) over the period of the conference, and each time, it performs a comparison with the threshold necessary for implementing a highly creative conference. In this operation example, a method (B) is used in which the value of TP is used for determination of creativity and the value corresponding to the central value of variation in evaluation value of creativity described in FIG. 5 is used as a threshold. Specifically, TP=100 ms^2.

In this operation example, autonomic nerve is adjusted in order to conduct a highly creative conference, for STEP 4 described above. Specifically, while the value of TP, which is continuously calculated every several seconds in STEP 4, is compared with the threshold every time 10 seconds elapse, creativity is determined whether it is high or low. In this operation example, the object to be determined is one participant with the highest value of TP in the determination every time. In the initial design, the execution time of STEP 4 is set to 15 minutes, and the number of implementations is set to 1 time. The time of individual menu of the conference program is not announced to participants, and it is announced and implemented that the conference program is completed in 2 hours as a whole time and time allocation of each menu is set each time. At this time, a conference time is about 1.5 hours in an initial conference program, and the total conference time is announced by adding the time for program adjustment of about 30 minutes. Using the time for adjusting this program, a program that makes a highly creative conference is designed. In addition, in a case where time is left when the conference is over, it may be determined at any time whether to perform free communication in that left time or to dissolve the conference early.

In a case of observing the transition of TP for 15 minutes in STEP 4 and measuring how much time exceeds the threshold for implementing a high creative conference, it is about 10%, the TP exceeds the threshold during the conference in some time zones, but the TP after 15 minutes is below the threshold. Therefore, since the designing unit 22 redesigns the conference time of STEP 4 to be 23 minutes, STEP 4 is extended by 8 minutes. The redesign of the conference by the designing unit 22 is calculated by extrapolating the value of TP after 15 minutes from the time change of TP for 15 minutes.

The redesign of the implementation conditions of the conference menu by the designing unit 22 is presented by the presentation unit 23. In this operation example, "the execution time of STEP 4 is 23 minutes" is presented to the smartphone or tablet PC carried by the moderator, as the redesign contents of the conference program. The moderator has the role of operating and managing the entire conference program, and the redesign contents are presented to the moderator in order for the participants to perform the dialogue without concern for the time.

The value of TP after executing STEP 4 for 23 minutes exceeds 100 ms^2 and the value of TP for eight minutes from 15 minutes to 23 minutes also exceeds the threshold for five minutes, so STEP 4 is completed at 23 minutes. (There is also a redesign that will be done twice instead of extending the time.)

3-2. Operation Example 2 (Extension of Time)

Next, another operation example of the present exemplary embodiment will be described. In this operation example, the preparation made in the above-described Operation Example 1 is arranged and the conference is started.

In a case of observing the transition of TP for 15 minutes in STEP 4 and measuring how much time exceeds the threshold for implementing a high creative conference, it is about 20%, TP exceeds the threshold during the conference in some time zones, but the TP after 15 minutes is below the threshold. Therefore, the designing unit 22 redesigns the conference time of STEP 4 to extend by five minutes. For the redesign of the conference by the designing unit 22, a method is implemented in which time extension is performed at predetermined time intervals until the value of TP exceeds the threshold and is repeated until a time zone during which TP exceeds the threshold for five minutes immediately before the scheduled end time reaches 50% or more. Although the extension time unit of this time is set to 5 minutes, this unit time is not limited to 5 minutes, and for example, the unit time is preferably about 5 minutes, at least as a measure of the time necessary to foster excitement of conversation. Since there is no need to end the conversation immediately after TP exceeds the threshold unless time is not enough, the time frame of the whole conference program may be adjusted within the time limit not exceeding two hours.

The redesign of the implementation conditions of the conference menu by the designing unit 22 is presented by the presentation unit 23. In this time, "extend the execution time of STEP 4 by five minutes" is presented to the smartphone or tablet PC carried by the participant with the highest TP, as the redesign contents of the conference program. The participants with high TP are likely to have the initiative in the conversation, and the flow of conversation is adjusted by announcing the timing of the end of the conversation.

The value of TP after executing STEP 4 for 20 minutes exceeds 100 ms^2 and the value of TP for five minutes from 15 minutes to 20 minutes also exceeds the threshold for three minutes, so STEP 4 is completed at 20 minutes. (There is also a redesign that will be done twice instead of extending the time.)

3-3. Operation Example 3 (The Number of Times Added)

Next, another operation example of the present exemplary embodiment will be described. In this operation example, the preparation made in Operation Example 1 is arranged and the conference is started.

In a case of observing the transition of TP for 15 minutes in STEP 4 and measuring how much time exceeds the threshold for implementing a high creative conference, it is about 5%, TP exceeds the threshold during the conference in some time zones, but the TP after 15 minutes is below the threshold. Therefore, the designing unit 22 redesigns that the number of conferences in STEP 4 is twice. The redesign of the conference by the designing unit 22 is continued until the value of TP exceeded the threshold or until the time zone exceeding the threshold reaches 50% or more. In addition, repeating the conference freely adjusted within a range where the entire conference program does not exceed time frame of 2 hours.

The redesign of the implementation conditions of the conference menu by the designing unit 22 is presented by the presentation unit 23. In this time, "the conference of STEP 4 is repeated once again" is presented to the smartphone or tablet PC carried by all the participants, as the redesign contents of the conference program. Since this instruction content is a notification to all the participants, an instruction related to the method of implementing the conference menu is also presented to the display installed at the position visible to the participants in the conference hall. Then, this instruction content is also presented as speech information to the hall by the moderator of a conference or a machine voice. This method is particularly effective in a case where participants are lost in conversation and have poor perception of image information or in a conference including a visually impaired person.

The value of TP after executing STEP 4 twice exceeds 100 ms^2, and the value of TP for second 15 minutes also exceeds the threshold at a time of 50% or more, so STEP 4 is completed in two rounds.

3-4. Operation Example 4 (Change of Constituent Members in Two Groups)

Next, another operation example of the present exemplary embodiment will be described. In this operation example, the preparation made in the above-described Operation Example 1 is arranged and the conference is started. However, the number of conference participants is eight (A, B, C, D, E, F, G, H), and in the conference of STEP 4, four people forms one group, and two groups (a red group: A, B, C, D and a blue group: E, F, G, H) perform conferences separately. Further, the TP determination is performed by the method (A) where the minimum value is used, the conditions are loose, and the objects to be determined are all participants.

In a case of observing the transition of TP for 15 minutes in STEP 4 and measuring how much time exceeds the threshold for implementing a high creative conference, it is about 5% in the red group and is about 15% in the blue group. However, both groups sometimes exceed the threshold during the conference in some time zones, but the TP after 15 minutes is below the threshold. At this time, as a result of measuring the value of TP of all the participants for each dialogue group, in the red group, A and B are likely to exceed the threshold. On the other hand, in the blue group, E and F are likely to exceed the threshold. The TPs of the other participants (C, D, G, H) hardly exceed the threshold.

In this case, even though there are participants who show high TP, there is a possibility that participants whose TP does not exceed the threshold are not only short of conference time but also have a problem such as interest in topics and affinity with people.

Therefore, the designing unit 22 redesigns the number of conferences in STEP 4 to be twice and the configuration of conference members to be changed. Specifically, considering the interest in topics and compatibility between participants having high TP and participants having low TP, a redesign is performed by combining the participants having low TP with another participant having high TP. Specifically, in this operation example, the members of the red group are A, B, G, H, and the members of the blue group are E, F, C, D. The redesign of the conference by the designing unit 22 is continued until the value of TP exceeded the threshold or until the time zone exceeding the threshold reaches 50% or more. In addition, repeating the conference freely adjusted within a range where the entire conference program does not exceed time frame of 2 hours.

The method of changing the progress plan of the conference is not limited to the change of the configuration of the conference members. For example, the change of the order of the conference items included in the conference, the replacement of the conference items, or the change of the time of the conference items may be performed. Further, in a case where there are plural changing methods of the progress plan, a changing method is determined according to the values of TP of participants. For example, in a case where the value of TP of the participant is less than the threshold and the differential value of TP is less than the threshold, the change of the participating members is adopted, while in a case where the value of TP of the participant is less than the threshold and the differential value of TP is equal to or greater than the threshold, extension of time may be adopted.

The redesign of the implementation conditions of the conference menu by the designing unit 22 is presented by the presentation unit 23. In this time, "The number of implementation of STEP 4 is set to twice, and the group organization is A, B, G, H for the red group, and E, F, C, and D for the blue group." is presented as the redesign contents of the conference program, to the smartphone or the tablet PC carried by the moderator. Since the moderator has the role of operating and managing the entire conference program, it is presented to the moderator in order to allow the participant to have a dialogue without concern for understanding the contents of the progress.

The value of TP after executing STEP 4 twice exceeds 100 ms^2, and the value of TP for second 15 minutes also exceeds the threshold at a time of 50% or more, so STEP 4 is completed in two rounds.

3-5. Operation Example 5 (Second Theme Change, High TP Determination)

In this operation example, the preparation made in the above-described Operation Example 1 is arranged and the conference is started. The TP determination is performed by the method (C) where the threshold is the highest value, and the object to be determined is the participant having the highest value among all participants.

In a case of observing the transition of TP for 15 minutes in STEP 4 and measuring how much time exceeds the threshold for implementing a high creative conference, it is about 5%, TP exceeds the threshold during the conference in some time zones, but the TP after 15 minutes is below the threshold. Therefore, the designing unit 22 redesigns that the number of conferences in STEP 4 is twice. The theme of the first conference is to promote discussion and ideas based on "past experiences", but the second time is redesigned to promote discussion and ideas based on the "current social environment". This is to consider the possibility that a difference in the degree of participation in a conference occurs depending on generations. Specifically, the older the participants, the easier it is to discuss based on the past experience, but the young generation, in extreme cases, elementary school students, have had little experience in the past, and may not be able to enter the conversation. Therefore, in order to eliminate the generation gap, it is devised to make the theme an agenda based on the "current social environment". The theme change is adjusted in various ways while determining the improvement of the TP, considering the generation and background information of participants.

The redesign of the conference by the designing unit 22 is continued until the value of TP exceeded the threshold or until the time zone exceeding the threshold reaches 50% or more. In addition, repeating the conference freely adjusted within a range where the entire conference program does not exceed time frame of 2 hours.

The redesign of the implementation conditions of the conference menu by the designing unit 22 is presented by the presentation unit 23. In this time, "Repeat the conference of STEP 4 once again by changing the theme" is presented to the smartphone or tablet PC carried by all the participants, as the redesign contents of the conference program. Since this instruction content is a notification to all the participants, an instruction related to the method of implementing the conference menu is also presented to the display installed at the position visible to the participants in the conference hall. Then, this instruction content is also presented as speech information to the hall by the moderator of a conference or a machine voice. This method is particularly effective in a case where participants are lost in conversation and have poor perception of image information or in a conference including a visually impaired person. The above effect can also be obtained by making notification to the moderator and announcing to the participants from the moderator.

The value of TP after executing STEP 4 twice exceeds 100 ms^2, and the value of TP for second 15 minutes also exceeds the threshold at a time of 50% or more, so STEP 4 is completed at the second time.

3-6. Operation Example 6 (Time Extension and TP Notification to Persons with Low TP)

The preparation made in Operation Example 1 is arranged and the conference is started. In a case of observing the transition of TP for 15 minutes in STEP 4 and measuring how much time exceeds the threshold for implementing a high creative conference, it is about 10%, the TP exceeds the threshold during the conference in some time zones, but the TP after 15 minutes is below the threshold. Therefore, since the designing unit 22 redesigns the conference time of STEP 4 to be 21 minutes, STEP 4 is extended by 8 minutes. The redesign of the conference by the designing unit 22 is calculated by extrapolating the value of TP after 15 minutes from the time change of TP for 15 minutes.

The redesign of the implementation conditions of the conference menu by the designing unit 22 is presented by the presentation unit 23. In this time, "the execution time of STEP 4 is 21 minutes" is presented to the smartphone or tablet PC carried by the moderator who has the role of operating and managing the entire conference program, as the redesign contents of the conference program. In addition, in order to raise the creativity of people with low TP, TP of that people is fed back together with other participants' TPs, which encourages active participation in the conference. This TP is presented to participants with lower TPs, with the individual names of other participants in a hidden state.

The value of TP after executing STEP 4 for 21 minutes exceeds 100 ms^2 and the value of TP for six minutes from 15 minutes to 21 minutes also exceeds the threshold for five minutes, so STEP 4 is completed at 21 minutes. (There is also a redesign that will be done twice instead of extending the time.)

3-7. Operation Example 7 (Arrange Autonomic Nerve Before Start of Conference by Meditation)

In this operation example, with respect to the conference menu (STEP 1) at the start of the conference, the conference support apparatus 20 designs the progress plan, in a design aspect in which the sympathetic activity is reduced, thereby guiding the sympathetic activity to be lowered when the conference is started.

In this operation example, the preparation made in Operation Example 1 is arranged and the conference is started. An average value (Method B) is used for TP determination. Prior to the start of the conference, participants are in tension in many cases. However, in order to conduct a highly creative conference, for example, it is desirable to finally improve TP, but as its preparation, it is desirable to suppress the sympathetic nerve once, that is, it is desirable to relax. Therefore, LF/HF is calculated as a substitute characteristic of the sympathetic activity by the calculation unit 21 from the biometric information measured when the conference is started. The value of LF/HF in the relaxed state is at least 20 or less, for example, 10 or less. In this time, with the threshold as 10, the value of all the participants before start of the conference, specifically, before STEP 1 is evaluated by the calculation unit 21. Before STEP 1, it is the time of orientation and greetings to explain the flow of the conference and notes on the day by the moderator. Originally, STEP 1 has a function of forming a safe and secure place to relieve tension. However, since there are concerns that this menu breaks the design which the menu named STEP 1 originally possesses in a case where autonomic nerve adjustment such as extension of time and repetition plural times is performed, it is effective to relieve tension as much as possible beforehand in order to conduct highly creative conference.

The value of sympathetic activity is evaluated by the maximum value in time change. The value is 11 for the participant A, is 15 for the participant B, is 30 for the participant C, and is 23 for the participant D. Therefore, since there are two participants (C and D) whose value of LF/HF is higher than the threshold 20, the presentation unit 23 presents additional introduction of meditation with suppression effect of sympathetic nerve for a predetermined time.

With respect to the suppression effect of sympathetic nerve by meditation, as shown in FIG. 11, individual differences are shown as variation (σ of standard deviation), but with reference to the central value this time, the meditation time is determined to be three minutes in order to suppress the maximum value 30 of LF/HF to 10.

The LF/HF values of the participants after finishing the meditation for three minutes are 7 for participant A, 8 for participant B, 10 for participant C, and 12 for participant D, respectively. Therefore, again, it is evaluated that all the participants satisfy the threshold. As a result, the designing unit 22 determines to start the conference program originally scheduled and transmits the design matter to the presentation unit 23. The presentation unit 23 presents an instruction "Please execute the scheduled conference program. First is STEP 1." to the smartphone or tablet PC carried by the moderator.

3-8. Operation Example 8 (Arrange Autonomic Nerve During the Conference with Yoga)

Even in this operation example, with respect to the conference menu (STEP 1) at the start of the conference, the conference support apparatus 20 designs the progress plan, in a design aspect in which the sympathetic activity is reduced, thereby guiding the sympathetic activity to be lowered when the conference is started.

In addition, in this operation example, the conference support apparatus 20 designs the progress plan of the conference (with respect to the conference items of STEP 2) in a design aspect in which the parasympathetic activity is increased, in a state where the sympathetic activity is suppressed.

Further, in this operation example, the conference support apparatus 20 designs the progress plan of the conference (with respect to the conference items of STEP 3) in a design aspect in which the sympathetic activity is increased, in a state where the parasympathetic activity is enhanced.

In this operation example, the preparation made in Operation Example 1 is arranged and the conference is started. In addition, it is assumed that the conference participants are E, F, G, H. An average value (Method B) is used for TP determination. Prior to the start of the conference, participants are in tension in many cases. However, in order to conduct a highly creative conference, for example, it is desirable to finally improve TP, but as its preparation, it is desirable to suppress the sympathetic nerve once, that is, it is desirable to relax. Therefore, LF/HF is calculated as a substitute characteristic of the sympathetic activity by the calculation unit 21 from the biometric information measured when the conference is started. The value of LF/HF in the relaxed state is at least 20 or less, for example, 10 or less. In this time, with the threshold as 20, the value of all the participants before start of the conference, specifically, before STEP 1 is determined. Before STEP 1, it is the time of orientation and greetings to explain the flow of the conference and notes on the day by the moderator. Originally, STEP 1 has a function of forming a safe and secure place to relieve tension. However, since there are concerns that this menu breaks the design which the menu named STEP 1 originally possesses in a case where autonomic nerve adjustment such as extension of time and repetition plural times is performed, it is effective to relieve tension as much as possible beforehand in order to conduct highly creative conference.

The value of sympathetic activity is evaluated by the maximum value in time change. The value of the participant E is 16, the value of the participant F is 29, the value of the participant G is 13, and the value of the participant H is 25. Therefore, since two participants (F and H) have the value of LF/HF higher than the threshold of 20, a conference program designing unit presents additional introduction of "twisting pose" to induce a relaxation mode in flexible exercise having suppression effect of sympathetic nerve. It is designed to perform the flexible exercises once at standard time of 30 seconds based on the relationship in FIG. 13.

With respect to the flexible exercises, the implementation method illustrated in FIGS. 12A and 12B is presented from the presentation unit 23 to all the participants by diagrams and explanations. The presented method is displayed on a large display set installed at the hall. The sympathetic activities after implementation of the flexible exercises are 8 for participant E, 19 for participant F, 7 for participant G, and 16 for participant H, respectively, and are lower than the threshold required to start STEP 1.

Next, after implementing the conference menu of STEP 1, evaluation is made about the parasympathetic nerve before implementation of STEP 2. STEP 2 is a menu for listening, which is expected to enhance the parasympathetic nerve. Here, the target value of the activity index HF before the start of STEP 2 is set to 50 ms^2. The values before start of STEP 2 are 45 ms^2 for participant E, 20 ms^2 for participant F, 39 ms^2 for participant G, and 27 ms^2 for participant H, respectively, and it is determined that the values of all the participants do not exceed the threshold. Therefore, the conference program designing unit presents additional introduction of "half tortoise pose" to induce a refresh mode in flexible exercises with enhancement effect of parasympathetic nerve. It is designed to perform the flexible exercises once at standard time of 30 seconds based on the relationship in FIG. 15.

With respect to the flexible exercises, the implementation method illustrated in FIGS. 14A and 14B is presented from the presentation unit 23 to all the participants by diagrams and explanations. The presented method is displayed on a large display set installed at the hall. The parasympathetic activities after implementation of the flexible exercises are 75 ms^2 for participant E, 56 ms^2 for participant F, 70 ms^2 for participant G, and 51 ms^2 for participant H, respectively, and exceed the threshold required to start STEP 2.

Next, after implementing the conference menu of STEP 3, the sympathetic activity before implementation of STEP 4 is evaluated. STEP 4 is a menu for conducting candid and open dialogue, which is expected to enhance sympathetic nerve. Here, the target value of the activity index LF/HF before the start of STEP 4 is set to 50. The values before the start of STEP 4 are 11 for participant E, 20 for participant F, 15 for participant G and 23 for participant H, and it is determined that the values of all the participants do not exceed the threshold. Therefore, the presentation unit 23 presents additional introduction of "antenna pose" to induce an energetic mode in flexible exercises with enhancement effect of sympathetic nerve. It is designed to perform the flexible exercises once at standard time of 30 seconds based on the relationship in FIG. 17.

With respect to the flexible exercises, the implementation method illustrated in FIGS. 16A and 16B is presented from the presentation unit 23 to all the participants by diagrams and explanations. The presented method is displayed on a large display set installed at the hall. The sympathetic activities after implementation of the flexible exercises are 55 for participant E, 65 for participant F, 58 for participant G, and 69 for participant H, respectively, and exceed the threshold required to start STEP 4.

Thereafter, STEP 4 is performed for 15 minutes. In a case of observing the transition of TP for 15 minutes in STEP 4 and measuring how much time exceeds the threshold for implementing a high creative conference, it is about 60%, TP is below the threshold during the conference in some time zones, but the TP after 15 minutes exceeds the threshold 100 ms$^2$. As a result, the conference program designing unit does not perform redesign, and the presentation unit 23 presents an instruction to proceed to the next STEP 5 as it is.

Meanwhile, in the related art, it is also proposed to calculate the time productivity of the conference by using the information on the voice and motion of the conference participant and to provide feedback. However, there are individual differences in the size of the voice, while actions such as nodding may also be performed reflexively, on the other hand, even in a case of listening silently, the degree of empathy may be increasing, and a state of high creativity does not always appear in speech and motion. In contrast, in the present exemplary embodiment, the biometric information of each of participants in the conference is measured, and the conference program is designed using the autonomic activity calculated using the measured biometric information. Specifically, in a case where the TP of the participant is low, it is changed to a program in which the TP is increased. Thus, the progress of the conference is supported so that the creativity of the conference is improved.

4. Modification Example

The above-described exemplary embodiments are merely examples of the present invention and may be modified as follows. In addition, the above-described exemplary embodiment and each modification described below may be implemented in combination as necessary.

(1) In the above exemplary embodiment, the conference support system 1 having the conference support apparatus 20 (example of the information processing apparatus) for supporting the conference has been described, but the information processing apparatus according to the present invention is not limited to an apparatus that supports a conference. For example, the information processing apparatus may be an apparatus that supports communication in a group place other than the conference, such as a place where a game is played by plural people.

(2) In the above-described exemplary embodiment, biometric information of each of participants is measured before the start of the conference and during the conference. The period during which the biometric information of the participant is measured is not limited to that described in the above-described exemplary embodiment. For example, the biometric information of the participant may not be measured before the start of the conference, and the measurement may be started after the conference is started.

(3) In the above-described exemplary embodiment, in a case where the measured TP value does not satisfy the predetermined condition, the conference program is changed. The designing method of the progress plan of a conference is not limited to that shown in the above-described exemplary embodiment. For example, the TP of the participant may be measured before the conference is started, and the conference program corresponding to the measured TP may be selected from a table in which a TP and a conference program are associated with each other. Further, for example, in a case where the autonomic activity calculated from the TP of the participant is less than a predetermined threshold, the conference support apparatus 20 may change the progress plan of the conference in a design aspect in which the autonomic activity is increased.

(4) In addition, in a case where an aspect of a change in the activity calculated from the TP of the participant satisfies a predetermined condition, the conference support apparatus 20 may change the progress plan of the conference. For example, the conference support apparatus 20 estimates whether or not the activity reaches a predetermined threshold, based on the aspect of a change in the calculated activity, and in a case where it is estimated that the activity reaches the threshold, the conference support apparatus 20 may change the progress plan of the conference in a manner of increasing the activity. Specifically, for example, in a case where the differential value of the calculated activity is equal to or more than the threshold, it is considered that the activity is rising, so in a case where the conference time is further extended, it is considered that the activity becomes higher. In that case, making changes to lengthen the time of the conference helps to increase the activity of the conference.

(5) In the present exemplary embodiment, the case where the conference program including the conference items of STEP 1 to STEP 5 is designed is exemplified, but the conference program to be designed is not limited to the one shown in the above-described exemplary embodiment. For example, other conference items may be included in the conference program.

(6) In the above-described exemplary embodiment, the program executed by the processor 252 of the conference support apparatus 20 may be downloaded through a communication line such as the Internet. In addition, these programs are provided in a state recorded in a computer-readable recording medium such as a magnetic recording medium (such as a magnetic tape and a magnetic disk), an optical recording medium (such as an optical disk), a magneto-optical recording medium, and a semiconductor memory.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An information processing apparatus comprising:
 a hardware processor, configured to:
  calculate autonomic activity of a participant, using biometric information measured by a measuring device that measures biometric information of the participant belonging to a group event at a group place;
  design a progress plan of communication of the group event at the group place in a design aspect corresponding to the calculated activity in which sympathetic activity is reduced; and
  present the designed progress plan.

2. The information processing apparatus according to claim 1,
 wherein in a case where the calculated activity is less than a predetermined threshold, the hardware processor changes the progress plan in a design aspect in which the activity is increased.

3. The information processing apparatus according to claim 2,
 wherein the hardware processor specifies at least one of time, number of repetitions, participants, or agenda of items included in the progress plan.

4. The information processing apparatus according to claim 1,
 wherein the hardware processor changes the progress plan, in a case where an aspect of a change in the calculated activity satisfies a predetermined condition.

5. The information processing apparatus according to claim 4,
 wherein the hardware processor estimates whether or not the activity reaches a predetermined threshold, based on the aspect of a change in the calculated activity, and in a case where it is estimated that the activity reaches the threshold, the hardware processor changes the progress plan in a manner of increasing the activity.

6. The information processing apparatus according to claim 5,
 wherein the hardware processor specifies at least one of time, number of repetitions, participants, or agenda of items included in the progress plan.

7. The information processing apparatus according to claim 4,
 wherein the hardware processor specifies at least one of time, number of repetitions, participants, or agenda of items included in the progress plan.

8. The information processing apparatus according to claim 1,
 wherein the hardware processor specifies at least one of time, number of repetitions, participants, or agenda of items of the group event included in the progress plan.

9. The information processing apparatus comprising:
 a hardware processor, configured to:
  calculate autonomic activity of a participant, using biometric information measured by a measuring device that measures biometric information of the participant belonging to a group event at a group place;
  design a progress plan of communication of the group event at the group place in a design aspect corresponding to the calculated activity in a design aspect in which parasympathetic activity is increased, in a state in which sympathetic activity is suppressed; and
  present the designed progress plan.

10. The information processing apparatus comprising:
 a hardware processor, configured to:
  calculate autonomic activity of a participant, using biometric information measured by a measuring device that measures biometric information of the participant belonging to a group event at a group place;
  design a progress plan of communication of the group event at the group place in a design aspect corresponding to the calculated activity in a manner of increasing the sympathetic activity, in a state in which parasympathetic activity is enhanced; and
  present the designed progress plan.

* * * * *